United States Patent
De Vincentiis et al.

(10) Patent No.: US 7,285,133 B2
(45) Date of Patent: Oct. 23, 2007

(54) ARTIFICIAL LARYNX

(75) Inventors: Marco De Vincentiis, Rome (IT);
Andrea Gallo, Rome (IT); Valentina Manciocco, Formello (IT); Vincenzo Marvaso, Rizziconi (IT)

(73) Assignee: Universita' Degli Studi Di Roma "La Sapienza", Rome (IT)

( * ) Notice: Subject to any disclaimer, the term of this patent is extended or adjusted under 35 U.S.C. 154(b) by 441 days.

(21) Appl. No.: 10/489,150

(22) PCT Filed: Sep. 12, 2002

(86) PCT No.: PCT/IB02/03714

§ 371 (c)(1),
(2), (4) Date: Mar. 10, 2004

(87) PCT Pub. No.: WO03/024365

PCT Pub. Date: Mar. 27, 2003

(65) Prior Publication Data

US 2004/0243234 A1    Dec. 2, 2004

(30) Foreign Application Priority Data

Sep. 12, 2001    (IT)    ............... RM2001A000554

(51) Int. Cl.
*A61F 2/20*    (2006.01)

(52) U.S. Cl. ........................................... 623/9

(58) Field of Classification Search ............ 623/9
See application file for complete search history.

(56) References Cited

U.S. PATENT DOCUMENTS 5,911,756 A    6/1999  Debry

OTHER PUBLICATIONS

International Search Report for PCT/IB02/03714, Filed Dec. 9, 2002.
Database WPI, Section PQ, Week 199422, Derwent Publications Ltd., London, GB; AN 1994-181056, XP002235501 & SU 1 801 414 A (Mosc Oncology Res Inst), Mar. 15, 1993.
Database WPI, Section PQ, Week 199422 Derwent Publications Ltd., London GB; AN 1994-181055 SP002235502 & SU 1 801 413 A (Mosc Oncology Res Inst), Mar. 15, 1993.
I. De Vincentiis, "Ulteriori risultati della sostituzione della laringe nel cane," Min O.R.L. 6, 260, 1956.
I. De Vencentiis and M. De Santis, "La replacement du larynx chez le chien avec prothese composee," Ann. Otoirayng. 73, 57, 1956.
I. De Vincentiis, "Primi tentativi della sostituzione della laringe nell'uomo," Arch. Ital. O.R.L. 81, 355, 1970.
I. De Vincentiis, D. Tropodi, G. Iannetti. R. Filippo, A. Bisemi, "La sostituzione della laringe dell'uomo," Valsalva 47.1.1970.
Marco de Vincentiis, MD; Antonio Minni, MD; Andrea Gallo, MD; Supracricoid Laryngectomy With Cricohyoidopexy (CHP) in the Treatment of Laryngeal Cancer:A Functional and Oncologic Experience, Laryngoscope 106; Sep. 1996, pp. 1108-1114.

*Primary Examiner*—Thomas Sweet
(74) *Attorney, Agent, or Firm*—Simpson & Simpson, PLLC

(57) ABSTRACT

An artificial larynx prosthesis (C) is object of the present invention, comprising: a first substantially ring-shaped element (A), taller in the back than in the front; a second pyramid-shaped element (B) placed, along its ridge, on the uppermost part of the first element, (A) so as to form what is substantially a single body. The prosthesis is a static crico-arytenoid unit that can be implanted in the forward region of the neck of a patient, who is subjected to total laryngectomy, between the patient's hypopharynx, trachea and esophagus.

17 Claims, 4 Drawing Sheets

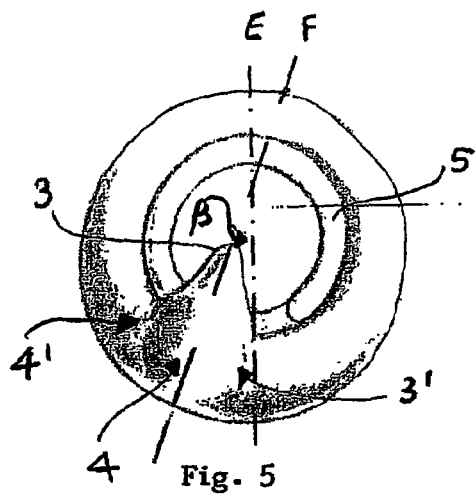
Fig. 5
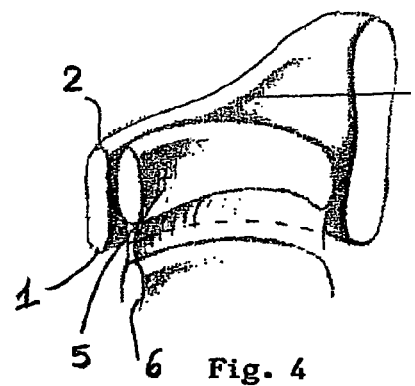
Fig. 4
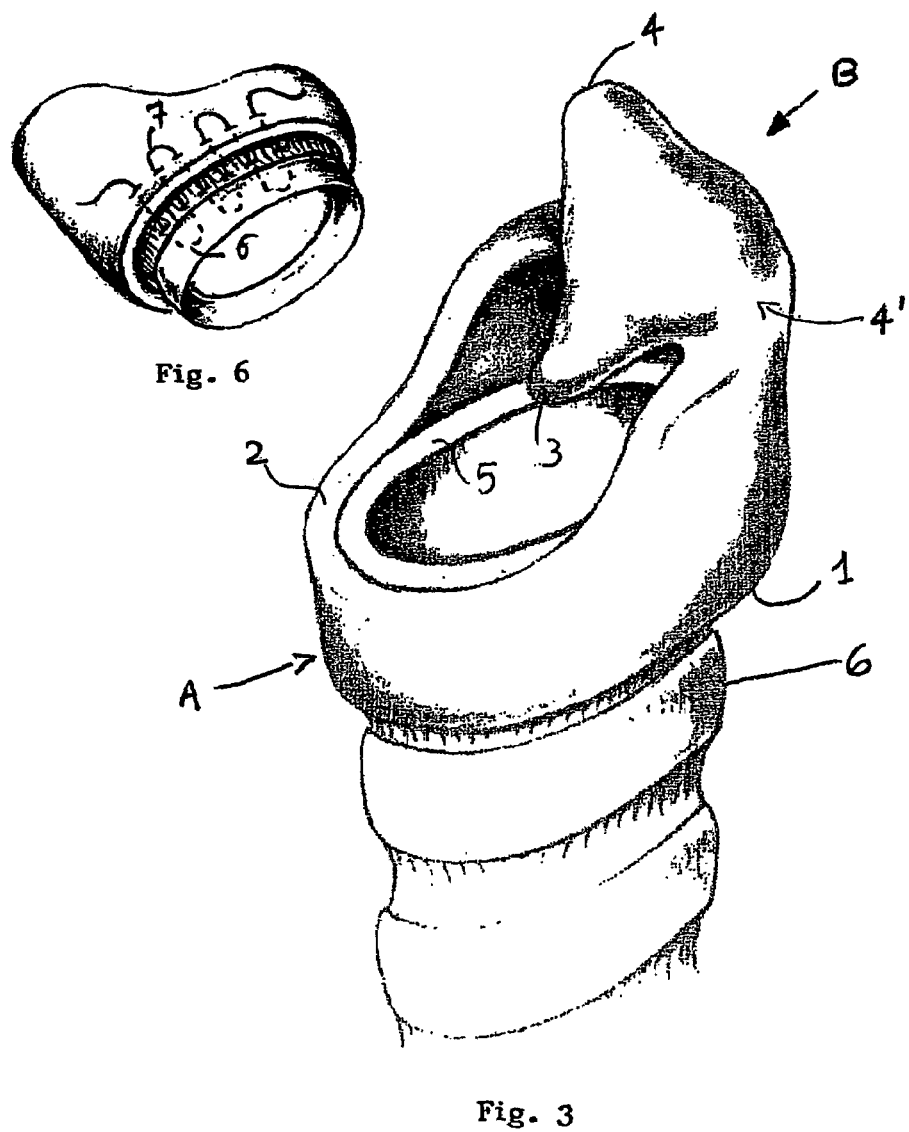
Fig. 6
Fig. 3

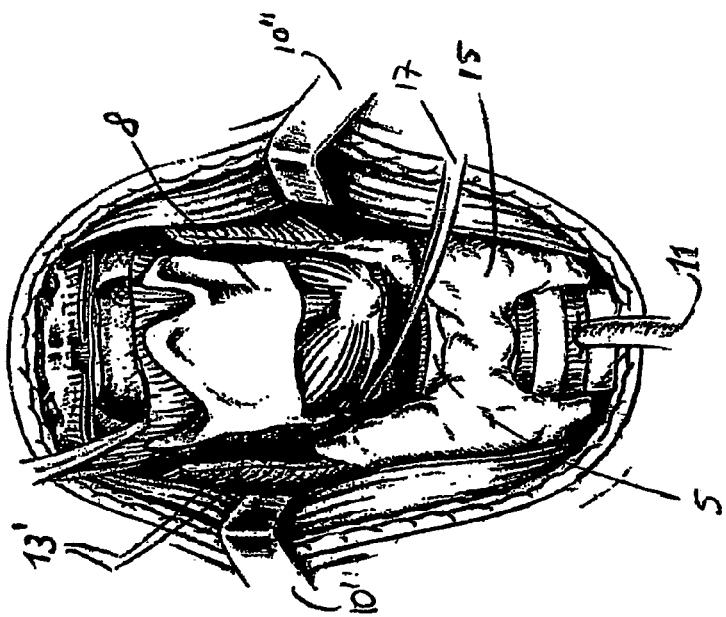
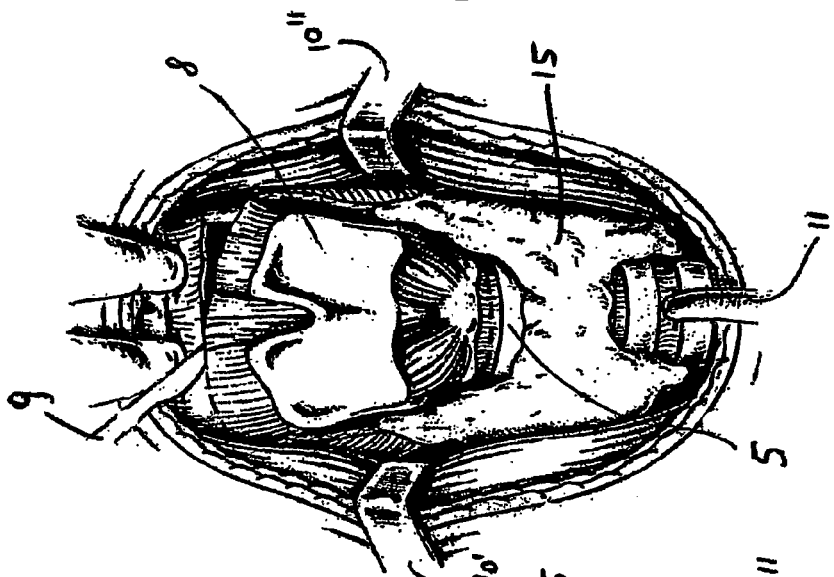
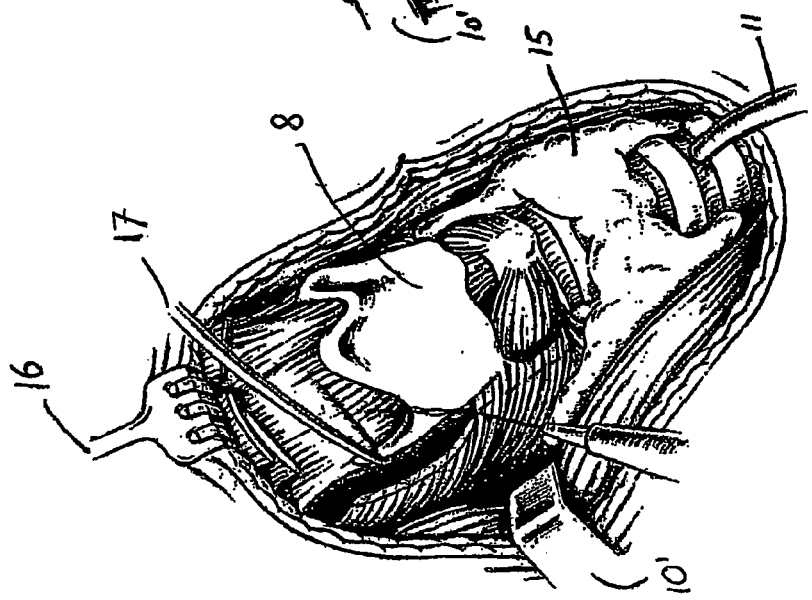
Fig. 9
Fig. 8
Fig. 7

ARTIFICIAL LARYNX

CROSS-REFERENCE TO RELATED APPLICATIONS

This application is the National Stage of PCT International Application No. PCT/IB2002/03714, filed Sep. 12, 2002; said international application claims priority from Italian Patent Application No. RM2001A000554, filed Sep. 12, 2001.

FIELD OF THE INVENTION

This invention refers to a laryngeal prosthesis or, more precisely, an artificial larynx, which can be manufactured from biologically compatible materials.

BACKGROUND ART

The human larynx has three basic functions that can be described as follows: deglutition (swallowing), respiration, and phonation (voice). Its most important part from a functional point of view is the crico-arytenoideus unit, which consists of the following:
- the fibrous cartilage structure constituted by the cricoid cartilage, the arytenoid cartilage, and the crico-arytenoideus articulation together with its capsule.
- muscle apparatus constituted by the crico-arytenoideus posticus and lateralis muscle.
- a vascular-nerve apparatus constituted by the recurrent nerve and the posterior inferior laryngeal artery.
- a flat cover consisting of the arytenois mucous membrane.

In particular, the cricoid is a rigid, ring-shaped cartilaginous structure; and the arytenoid is a rigid, triangular cartilaginous structure situated above the cricoid cartilage and articulated with it, forming the crico-artenoideus unit.

The three primary functions of the larynx are based on the aforecited elements:
- Respiration is provided by the rigid, ring-shaped cricoid cartilage.
- Phonation (voice) is obtained by the production of sounds that originate in the windpipe through which air is expirated situated at the base of the tongue and the arytenoid.
- Deglutition (swallowing) is accomplished by the sphincteral action of the arytenoid unit, provided that the tongue retropulsion and larynx elevation functions remain intact.

The most common health conditions that lead to the need for surgery to remove the larynx, in whole or in part, involve tumors.

Restoration in an artificial manner of the physiological functions associated with the larynx that has been removed represents an objective that for over a century has challenged otorhinolaryngologists. Ever since 1876, recourse has been made to ablation of the stoma (opening) which, by its very nature, represents the greatest limit to social re-integration of a patient who has undergone a total laryngectomy.

In 1956 (I. De Vincentiis, "Ulteriori risultati della sostituzione della laringe nel cane," Min O.R.L. 6, 260, 1956; I. De Vencentiis and M. De Santis, "La réplacement du larynx chez le chien avec prothèse composeé," Ann. Otoirayng. 73, 57, 1956) experiments were conducted on a dog, replacing its larynx with a polyethylene tube reinforced externally with steel and Vitallium wires or threads. At a later time (I. De Vincentiis, "Primi tentativi della sostituzione della laringe nell'uomo," Arch. Ital O.R.L. 81, 355, 1970; I. De Vincentiis, D. Tropodi, G. lannetti. R. Filippo, A. Bisemi, "La sostituzione della laringe dell'uomo," Valsalva 47.1.1971), a first effort was made to use a prosthetic replacement of a human larynx, using a white dacron tube reinforced with Vitallium rings. However, the swallowing difficulties that ensued made it necessary, after little more than a month, to proceed to a conventional, total laryngectomy.

In recent years, surgery of the larynx has evolved considerably from an approach based on demolition to one that is more conservative. Functional laryngeal surgery involves a whole series of operating techniques, put into practice in case of neoplastic disease, aimed at preserving the functions of the vocal organ to the greatest extent possible. In cases of neoplastic disease, functional laryngeal surgery is identified with the techniques of partial and sub-total laryngectomy. The objective of sub-total surgery is to obtain a "neo-larynx" that is valid from a functional standpoint. This means rebuilding a new vocal organ that is capable of carrying out the three vital functions of the larynx, i.e., respiration, deglutition, and phonation.

The surgical techniques of sub-total laryngectomy, described in De Vincentiis et al., "Supracricoid Laryngectomy with Cricohyoidopexy (CHP) in the Treatment of Laryngeal Cancer: A Functional and Oncological Experience," Laryngoscope 106:1108-1114, 1996, involve the following:
- Subtotal laryngectomy with preservation of two-thirds of the epiglottis and one or both arytenoid cartilages: Crico-hyoido-epiglotto-pexy (CHEP) according to Mayer-Piquet, which represents an alternative to partial surgery.
- Subtotal laryngectomy with preservation of one or both arytenoid cartilages: Crico-hyoido-pexy (CHP), according to Labayle, which represents an alternative to total surgery.

Both of the foregoing techniques call necessarily for the preservation of both the cricoid ring and at least one of the arytenoid units, as these represent the minimum elements necessary for reconstruction of the crico-arytenoid unit and serve as the basis for the rehabilitation of patients who have undergone sub-total surgery.

The cornerstone of this reconstructive surgery is represented by the "crico-arytenoid unit", on which a large part of the functional recovery of the neo-larynx is based.

From a surgical point of view, the maintenance of this structure is of primary importance. To this end, during surgery it is necessary to respect the vascular-nerve peduncle and the arytenoid mucous cap. Early mobilization of the arytenoid avoids the insurgence of a fibrosis of the crico-arytenoid articulation, which would lead to functional failure of the surgery and would require a total laryngectomy, not for oncological reasons but motived solely by the functional inadequacy of the neoglottis.

Movement of the crico-arytenoid unit, whose parts have been described above, takes place basically along two lines:

a) Vertical movement, caused by the crico-arytenoideus posticus muscle which, by pulling down and backward on the muscle apophysis, makes the arytenoid rotate in a circular movement upwards and outwards, opening the laryngeal neo-lumen. Relaxation of this muscle makes the arytenoid lean forward (a movement referred by Bonnet as the "arytenoid bow or nod").

b) Horizontal movement, caused by the lateral crico-arytenoideus muscle which, by pulling down and forward on the muscle apophysis, causes a rotation inwards of the arytenoid, leading to closure of the laryngeal lumen.

That closing movement of the neo-glottis is thus achieved by rotation of the arytenoid body forward, downward, and inward, as a result of contraction of the lateral crico-arytenoideus muscle and relaxation of the crico-arytenoideus posticus muscle. The opposite takes place for opening the neo-glottis (relaxation of the lateral crico-arytenoideus muscle and contraction of the crico-arytenoideus posticus muscle.

At the present time, thanks to progress made in surgical techniques and, even more particularly, to the public being made more aware about prevention, recourse to total laryngectomies is becoming less and less frequent. Nevertheless, there are still a significant number of patients for whom this operation becomes necessary. And in these cases, despite the contribution of modern rehabilitation techniques, it has not been possible to get satisfactory results in terms of social recovery of the patients. Indeed, even when:

resumption of deglutition (swallowing) is good;
resumption of phonation (voice function) can be obtained by creating phonic fistulas (air passage between the trachea and the esophagus, in some cases inserting a valve when there is incontinence during swallowing), or by training the patient to coordinate the vibration of the hypopharyngeal mucous produced by the air swallowed into the stomach (esophagal voice);

it is nevertheless true that:

resumption of respiration by natural means still constitutes a problem. As a matter of fact, all efforts to connect the trachea directly to the base of the tongue have failed, because the posterior membranous part of the trachea is not rigid enough to sustain a lumen sufficiently wide for satisfactory respiratory function. It is therefore clear that, even though the procedure may apply to an ever smaller number of patients, the problems connected with total a laryngectomy have not been resolved.

A study has now been made and an artificial laryngeal prosthesis designed that will make it to possible for patients who have undergone a total laryngectomy to recover socially and to overcome the problems described above.

SUMMARY OF THE INVENTION

It is an object of the present invention to obtain creation of a prosthesis consisting of an artificial larynx.

Another object is to obtain an artificial larynx that allows for resumption of the basic natural laryngeal functions, i.e., deglutition, respiration, and phonation. Still another object is to obtain an artificial larynx made of materials that are biologically compatible and that may have been treated so as to increase their biological compatibility.

A further object is the use of such materials to build the larynx according to the invention.

Additional objects of the invention will appear evident in the following detailed description of the invention itself.

BRIEF DESCRIPTION OF THE FIGURES

The figures must be understood to be illustrative and do not in any way limit the scope of the invention.

FIG. 3 is a view in perspective of another embodiment of the prosthesis according to the invention in which the prosthesis is place on the tracheal stump.

FIG. 4 is a partial side view of the prosthesis of FIG. 3.

FIG. 5 is a view from above of the prosthesis of FIG. 3.

FIG. 6 is a view in perspective, as seen from below, of the prosthesis of FIG. 3, mounted on the terminal part of the tracheal stump.

FIG. 7 is a view of the operating field during one of the phases of a total laryngectomy.

FIG. 8 is a view as in FIG. 7, but of a later phase of a total laryngectomy.

FIG. 9 is a view as in FIG. 7, but of an advanced phase of a total laryngectomy.

DETAILED DESCRIPTION OF THE INVENTION

It is the scope of the present invention to restore, in an artificial manner, the physiological functions of the larynx that were suppressed by the total laryngectomy.

The invention thus concerns an artificial larynx based on a substantially "static" crico-arytenoid unit that is implanted in the forward region of the neck between the hypopharynx, the trachea, and the esophagus.

The parts that make up the prosthesis, (C), according to the invention are the following:

1) A first element, (A), basically ring-shaped, with an internal lumen substantially circular, taller in the back than in the front, which reproduces the natural cricoid cartilage.

2) A second element, (B), which is substantially tetrahedral or pyramid shaped (pyramid with triangular base and apices or vertices (3, 4, 3', 4')), such second element reproduces the natural arytenoid cartilage, and is placed, along its ridge, on the uppermost part of the first element, (A), so as to form what is substantially a single body that constitutes the prosthesis, (C), of the invention.

With reference to the figures, the first element, (A), has a lower edge, (1), that lies essentially on an horizontal base plane, (D), perpendicular to the longitudinal axis of the trachea, and an upper edge, (2), which is of variable height with respect to the aforementioned horizontal plane, (D), in such a way that two areas are formed, opposite each other, one of minimum height and another of maximum height, joined together in a substantially uniformly variable manner. The element (A) is further provided with a symmetry plane (E), which is perpendicular to plane (D). The second element, (B), connected to element (A) at its own ridge, has the advantage of having the free apices, (3) and (4), directed towards the inside of element (A), with apex (3) facing the median axis and forward, partially occupying the internal part of the first element, (A).

Figure 1A:
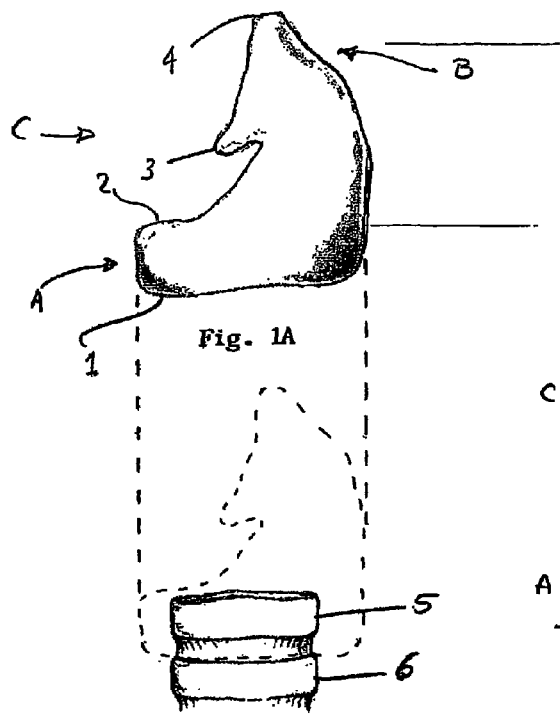
FIG. 1A is a lateral view of the of the prosthesis, (C), according to the invention.
Figure 1D:
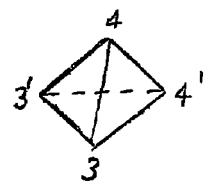
FIG. 1D is a very schematic view of the geometric figure (tetrahedron/triangular pyramid) to which the element (B) of the prosthesis is comparable of the invention.

FIG. 1D shows a very approximate schematic rendition of element (B), whose shape, as said in the above, is basically that of a regular triangular pyramid or tetrahedron but with rounded edges and vertices. On this pyramid we can see the aforementioned apices, (3) and (4), and apices (3', 4') on the connecting ridge of element (A).

Figures 1B, 1C:
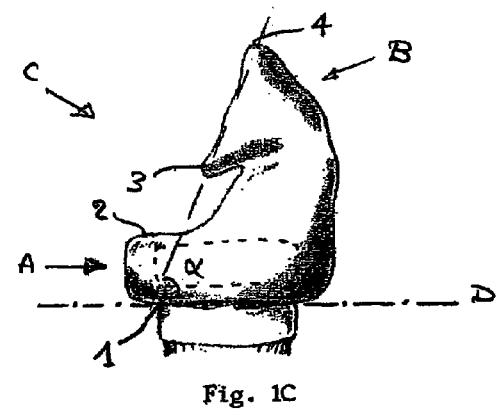
FIG. 1B is the prosthesis of FIG. 1A, shown by a dotted line, positioned on the tracheal stump.
FIG. 1C is a view as in FIG. 1B, in which it is shown by a dotted line the part of tracheal stump on which the prosthesis is positioned.
Figure 2A:
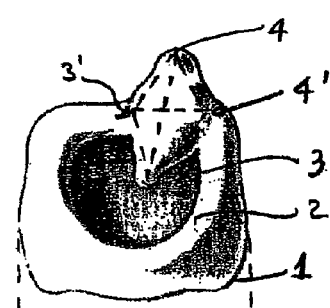
FIG. 2A is a frontal view of a first embodiment of the prosthesis of the invention.
Figure 2B:
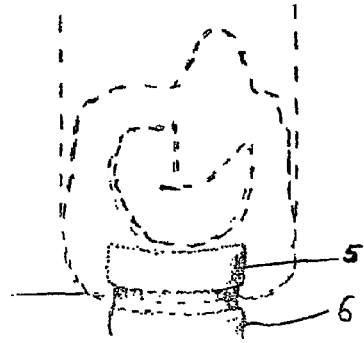
FIG. 2B is the prosthesis of FIG. 2A, shown by a dotted line, positioned on the tracheal stump.
Figure 2C:
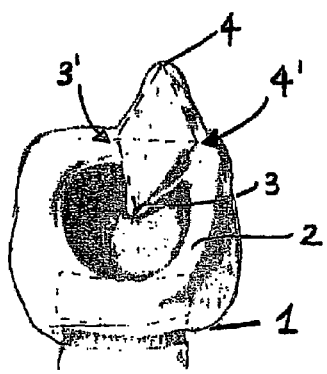
FIG. 2C is the view of FIG. 2B in which it is shown by a dotted line the part of tracheal stump on which the prosthesis is positioned.

Preferably the edge that has at its two extremities apices (3) and (4) and that is opposite the edge that the second element, (B), has in common with the first element, (A), is slanted so as to form an α angle with respect to the horizontal plane (D). This α angle ranges between 20° and 70°, preferably between 30° and 40° (see FIG. 1C).

Preferably, as for example illustrated in FIG. 5, the thickness of ring element (A) varies, in the sense that the thickness of the back part, i.e., that involving the area where element (B) is positioned, is greater than the thickness of the front part that stands opposite to it.

FIGS. 1A, 1B, 1C, 2A, 2B, and 2C show a ring shape for the prosthesis that is an alternative to that shown in FIGS. 3-8. This shape is that of an irregular ring, with the external perimeter of element (A) generically quadrangular with respect to the circular internal lumen. Element (B) too is irregular. These irregularities represent an advantage for anchoring the prototype to the tracheal stump.

The prosthesis, (C), is implanted on the tracheal stump of patients subjected to a laryngectomy. It is preferable that it be implanted on the first free ring of the trachea, (5), as shown better in FIG. 6, where the suture thread is indicated as (7). It is also preferable, with particular reference to FIG. 5, that the prosthesis, (C), be mounted on the tracheal stump ring, (5), in an asymmetrical manner, that is, so that plane (F), identified by the ridge of element (B), bearing the apices (3, 4) and by the median point of the connecting ridge with element (A) (the one bearing apices (3', 4')), forms an approximately 30°-50° β angle with the symmetry plane (E), said plane (E) corresponding to the median plane of the human body. According to a preferred embodiment, the prosthesis is asymmetrical, that is, the element (B) is placed on the highest part of element (A), in such a way that plane (F), identified by the ridge of element (B) having apices (3) and (4) and by the median point of the ridge connecting it with element (A), forms an approximately 30°-50°β angle with the symmetry plane (E) of the element (A).

The size of the prosthesis is substantially the same as that of the natural larynx removed during surgery. It is preferable that the first, ring-shaped element, (A), have the following dimensions: front height: approx. 6-7 mm; rear height: approx. 21-23 mm; front thickness: approx. 2 mm; rear thickness: approx. 5 mm; lateral thickness: approx. 3 mm; inner diameter approx. 5-60 mm; outer diameter. approx. 10-65 mm; total weight: approx. 200-450 mg.

Preferably the second, pyramid-shaped element, (B) should have the following dimensions: height: approx. 18 mm; length: approx. 14 mm; average thickness: approx. 9 mm.

The prosthesis, (C), obtained by combining elements (A) and (B), has the following overall measurements: maximum height at the summit (4): approx. 34-35 mm; length from the upper edge (2) of the first element, (A), to the free apex (3) of the second element, (B): approx. 12 mm; length from the upper edge (2) of the first element (A) to the point of joining between the two elements, (A) and (B): approx. 20 mm; average weight: approx. 300-600 mg.

Materials that can be advantageously used to build the prosthesis according to the invention are all those materials that are biologically compatible or artificially biological, modified and/or treated so as to be biologically compatible. They are also selected in order to have the mechanical characteristics necessary to make them suitable for making artificial cartilage. In particular, appropriate substances comprise one or more natural or synthetic polymer materials, which may have been modified, such as the ones listed in the following: polythenes, polypropylenes, polyvinyl chlorides, polyamides, polymethyl methacrilates, polyvinyl fluorides, polyvinylidene fluorides, polytetrafluoroethylenes, polyvinyl alcohols, polyethylene oxides, polyurethane, polyvinyls, proteoglycans, chitosans, polysaccharides, polyvinylpyrrolidones, propriolactic acid polymers, all of which may be suitably modified and/or made functional, may be combined with each other and/or with additives to make them more plastic, stable, and compatible, or still other additives that improve their characteristics for the given purpose.

The polymer materials may be used in the form of fabrics, threads, non-woven fabrics, casting, film, and combinations thereof.

The prosthesis according to the invention reproduces a fixed crico-arytenoid unit that is intended to restore the physiological functions of the larynx (deglutition, respiration, and phonation).

To this end, the prosthesis is positioned in correspondence with the anatomical seat that housed the larynx of the patient prior to its surgical removal, that is, in the frontal region of the neck between the hypopharynx above and to the back of it and the trachea below it. The procedure for implanting the prosthesis may be of a primary or secondary type.

In the case of primary implant, the total laryngectomy and the positioning of the prosthesis take place during the same surgical operation. This can be schematically described in two phases:

1) subtotal laryngectomy, shown in FIGS. 7, 8, and 9.

Figure 11:
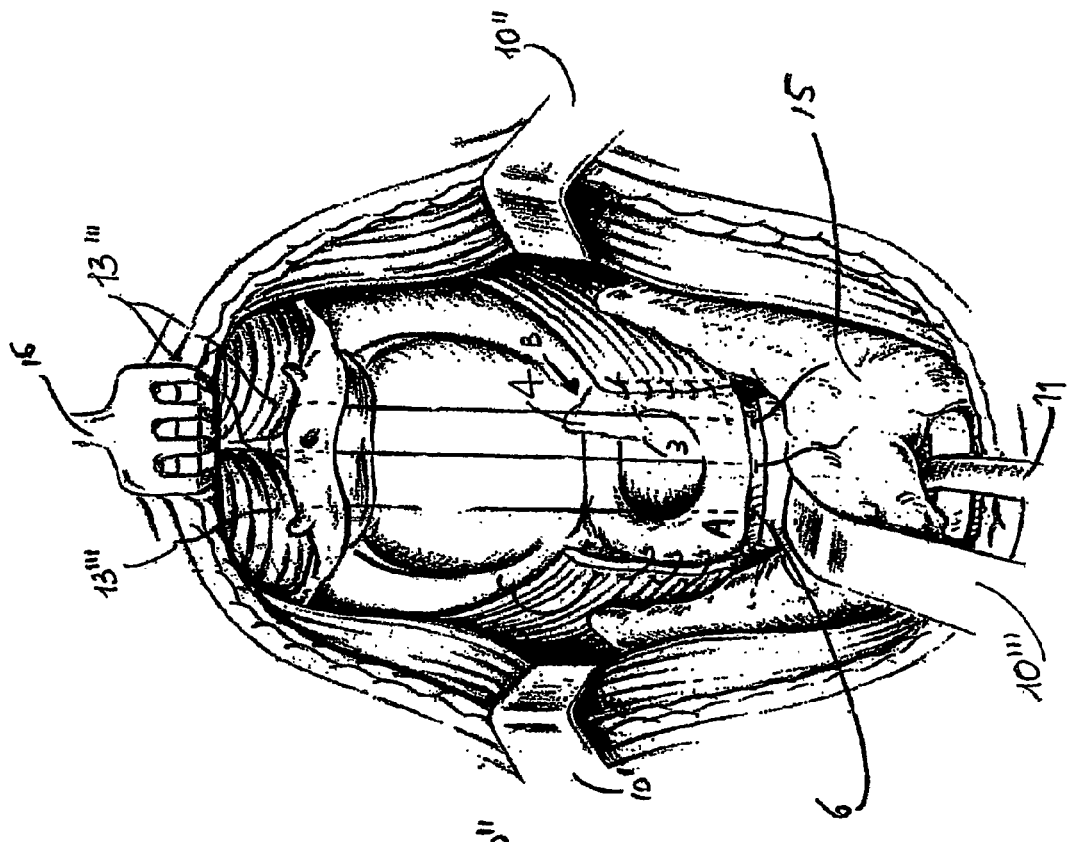
FIG. 11 is a view as in FIG. 7, but with the prosthesis of the invention completely inserted.
Figure 10:
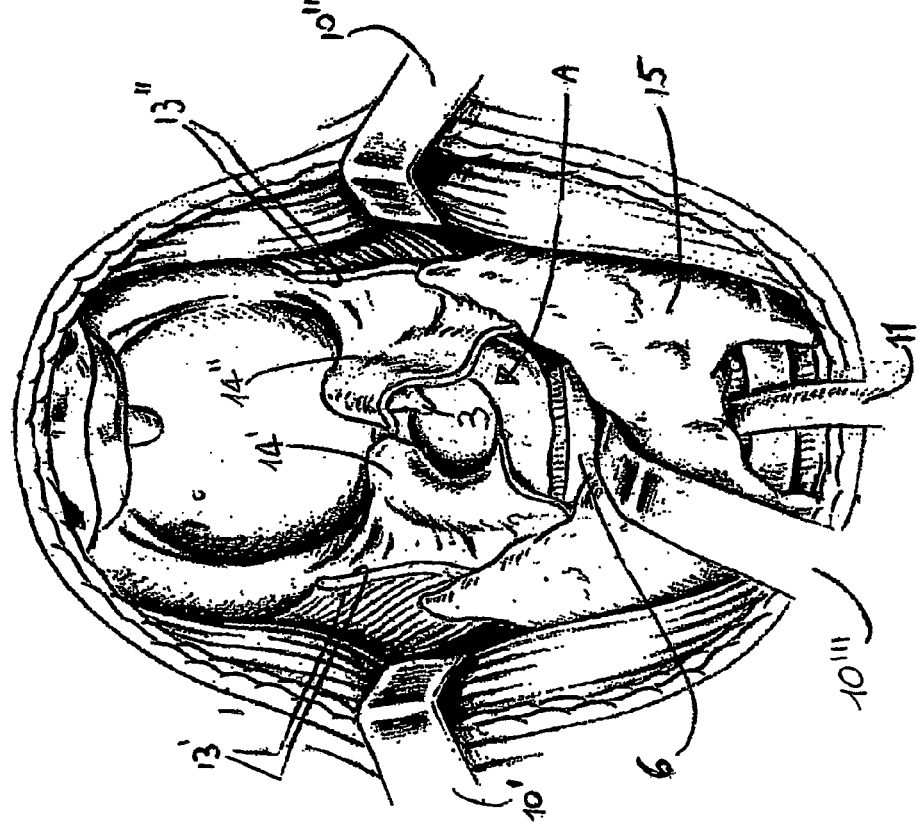
FIG. 10 is a view as in FIG. 7, but with the prosthesis of the invention partially inserted.

2) positioning of the prosthesis, shown in FIGS. 10 and 11.

So as to facilitate their interpretation by an expert in the field, the elements identified in FIGS. 7 through 11 are the following:

(8) thyroid cartilage, (9) scalpel, (10', 10", 10''') retractor and tape, (11) endotracheal ventilating prosthesis, (12) scissors, (13', 13") suture thread on the constrictor muscle, (13''') suture thread, (14', 14") edge of hypopharyngeal mucous, (15) thyroid gland, (16) multiple-hook retractor, and (17) single-hook retractor.

With reference to FIGS. 7 through 11, the removal of the larynx is carried out making every effort to preserve the prelaryngeal muscles (if oncologically possible) and, obviously, the hyoid bone (in some very special cases it is possible to remove this, being careful however to include in the joining at least 2 to 3 centimeters of the base of the tongue).

FIG. 7 shows the outline of the section (or better, of detachment-disinsertion of the lower, median, and upper constrictor muscles). It also shows how it is necessary, in order to make the joining more consolidated, to make sure the thyroid gland remains intact (16), which will permit adequate vascularization of the first tracheal rings and thus optimize the joining.

FIGS. 8 and 9 show the outline of the section on a subhyoid level, which permits access to the glosso-epiglottic vallecula and, at the same time, the beginning of the section of the larynx from top to bottom. Clearly shown is the level of the tracheostomy, modulated according to the requirements of the surgery and of the "tension" of the joining. When the operating field has been freed, the surgeon proceeds to insert the prosthesis that has been invented (C), fixed with suture thread (7) (FIG. 5) to the tracheal stump above the second-to-last ring (6).

FIG. 10 shows the phase during which the prosthesis, (C), of the invention is covered, by covering the arytenoid zone (first element (A) of the prosthesis, (C), of the invention) and the cricoid edge (second element (B) of the prosthesis, (C), of the invention) with the edges, (14' and 14"), of the mucosa in the lateral hypopharyngeal region.

FIG. 11 shows the phase during which the prosthesis, (C), of the invention is covered externally with the prelaryngeal muscles and the thread necessary for joining is in position.

Once the total laryngectomy has been performed, the surgeon will "modulate" the height of the tracheotomy, which should be at least 2 rings below the lower tracheal limit of the exeresis.

The trachea is raised so that the first tracheal ring, (5), can be inserted inside the larynx prosthesis, (C), so that the trachea is in contact with the inner walls of the prosthesis itself. Externally, the prosthesis will be covered with the upper, median, and lower pharyngeal constrictor muscles. Then the edge of the hypharyngeal mucous, (14', 14"), will be attached to the lateral and median edge of the highest portion of the prosthesis (upper vertex) in such a way as to create a mucous cap covering the vertex of the prosthesis. Lastly, the surgeon will perform the neolaryngo-hyoidopexy, i.e., the joining between the prosthesis, (C), and the hyoid bone.

In the case of secondary implant, the operating field will be represented by the consolidated results of the total laryngectomy.

The surgeon will then proceed to dissection of the trachea for at least 4 or 5 rings from the cutis of the stoma opening), after which he will carry out a new tracheotomy 3-4 rings below the edge of the stoma proper. Externally, the prosthesis will be covered with the upper, median, and lower pharyngeal constrictor muscles freed of scar adhesions. The cervical edge will be detached, exposing the hypopharynx, which will then be opened medially. Part of the hypopharyngeal mucous, made to slip onto the medial and lateral edge of the prosthesis, will be utilized to cover the neo-arytenoid. The last procedure is the "neolaryngo-hoidopexy".

Patients who are to receive the prosthesis according to the invention are those for whom it has not been possible, for oncological reasons, to preserve the cricoid during subtotal laryngectomy, and those who have been subjected to a total laryngectomy.

The prosthesis reproduces a substantially static crico-arytenoid unit with the arytenoid in a paramedian position, implantable in the forward region of the neck of a patient, subjected to a total laryngectomy, between the patient's hypopharynx, trachea, and esophagus.

Compared with existing products for the same field of application, the prosthesis of the invention has the advantage of permitting restoration of the laryngeal functions and definitive closure of the tracheostomy.

The minimum characteristics that are indispensable for implanting the prosthesis are the following:

a) Preservation of the hyoid bone, if oncologically possible.

b) Exeresis not extending beyond the $2^{nd}$ or $3^{rd}$ tracheal ring.

c) Preservation of a sufficient amount of hypopharyngeal mucous to cover the prosthesis.

Basically, excluded in principle from the primary application of the prosthesis are the following cases: tumors having particular subglottis extension; pyriform breast tumors; and very extensive tumors of the base of the tongue. Excluded in principle from secondary application of the prosthesis are the following cases: tumors having particular subglottis extension; very extensive tumors of the base of the tongue, even though in this case it would be possible to hypothesize an implant at a later date, since hypertrophy of the tongue muscles might then permit an implant.

The invention claimed is:

1. Artificial larynx prosthesis, (C), that can be implanted on the stump of a trachea, comprising:
   a first, substantially ring-shaped element, (A), said ring-shaped element comprises a substantially circular internal lumen having a lower edge (1), that lies essentially on a flat base, (D), and an upper edge (2) which is of variable height with respect to said flat base (D), in such a way that two areas, one forward area of minimum height and one back area of maximum height are formed opposite each other and joined together in a gradual incline, wherein said flat base is perpendicular to a longitudinal axis of the first, substantially ring-shaped element, and the first, substantially ring-shaped element (A) further comprises a symmetry plane (E), which is perpendicular to said flat base (D);
   a second pyramid-shaped element, (B), comprising a triangular base and first, second, third and fourth apices (3, 4, 3', 4'), wherein said third and fourth apices (3', 4') form a first ridge, said second pyramid-shaped element is positioned along said first ridge on the back area of the first, substantially ring-shaped element, (A), wherein said first, substantially ring-shaped element and said second pyramid-shaped element form a single unit, the first and second apices (3, 4) of said second pyramid-shaped element (B) being directed towards the inside of the first, substantially ring-shaped element (A), with said first apex (3) facing the median axis and forward of the first, substantially ring-shaped element (A).

2. Prosthesis according to claim 1, wherein said first and second apices (3, 4) form a second ridge, said second ridge and a median point of said first ridge form a plane (F), and the second pyramid-shaped element (B) is positioned in the back area of the first, substantially ring-shaped element (A) in such a way that said plane (F) forms an approx. 30°-50° β angle with respect to the symmetry plane (E).

3. Prosthesis according to claim 1, wherein said prosthesis constitutes a substantially static crico-arytenoid unit that can be implanted in the forward region of the neck of a patient, who is subjected to total laryngectomy, between the patient's hypopharynx, trachea, and esophagus.

4. Prosthesis according to claim 3, wherein said prosthesis is adapted to be implanted on the first free ring, (5), of the trachea.

5. Prosthesis according to claim 4, wherein said first and second (3, 4) apices form a second ridge, said second ridge and a median point of said first ridge form a plane (F), and said prosthesis is adapted to be implanted on the first free ring, (5), of the trachea in an asymmetrical manner in such a way that said plane (F) forms an approx. 30°-50° β angle with respect to the symmetry plane (E).

6. Prosthesis according to claim 1, wherein said first and second apices (3, 4) form a second ridge, said second ridge forms an α angle of 20° to 70° with said flat base (D).

7. Prosthesis according to claim 6, wherein the α angle ranges between 30° and 40°.

8. Prosthesis according to claim 1, wherein an outer perimeter of the first, substantially ring-shaped element (A) is quadrangular with respect to the circular internal lumen.

9. Prosthesis according to claim 1, wherein the a thickness of the first, substantially ring-shaped element (A) is variable in the sense that a thickness of the back area is greater than a thickness of the front area.

10. Prosthesis according to claim 1, wherein the first, substantially ring-shaped element (A) comprises the following measurements: a front height: approx. 6-7 mm; a rear height: approx. 21-23 mm; a front thickness: approx. 2 mm; a rear thickness: approx. 5 mm; a lateral thickness: approx. 3 mm; an internal diameter: approx. 5-60 mm; an external diameter: approx. 10-65 mm; a total weight: approx. 200-450 mg.

11. Prosthesis according to claim 1, wherein the second pyramid-shaped element (B) comprises the following measurements: a height: approx. 18 mm; a length: approx. 14 mm; an average thickness: approx. 9 mm.

12. Prosthesis according to claim 1, wherein the prosthesis, (C), obtained by combining the first, substantially ring-shaped element (A) and the second pyramid-shaped element (B), comprises the following measurements: a maximum height at said second apex (4): approx. 34-35 mm; a length from upper edge (2) of the first, substantially ring-shaped element (A) to said first apex (3) of the second pyramid-shaped element (B): approx. 12 mm; a length from upper edge (2) of the first, substantially ring-shaped element (A) to a point of fusion between the first, substantially ring-shaped element (A) and the second pyramid-shaped element (B): approx. 20 mm; an average weight: approx. 300-600 mg.

13. Prosthesis according to claim 1, wherein a material that is used to build the prosthesis is a biocompatible material.

14. Prosthesis according to claim 13, wherein the biocompatible material is selected from the group consisting of: polythenes, polypropylenes, polyvinyl chlorides, polyamides, polymethyl methacrilates, polyvinyl fluorides, polyvinylidene fluorides, polytetrafluoroethylenes, polyvinyl alcohols, polyethylene oxides, polyurethanes, polyvinyls, proteoglycans, chitosans, polysaccharides, polyvinylpyrrolidones, propriolactic acid polymers, combinations thereof, and combinations of at least one of said selected material with at least one additive capable of making said at least one of said selected material more plastic, stable, compatible or improve said at least one of said selected material's characteristics for the given purpose.

15. Prosthesis according to claim 13, wherein the biocompatible material is used in a form selected from the group consisting of: fabrics, threads, non-woven fabrics, casting, film, and combinations thereof.

16. Prosthesis according to claim 1, wherein said prosthesis is adapted to reproduce a substantially static cricoarytenoid unit and is adapted to restore the basic physiological functions of the larynx, which are the following: deglutition, respiration, and phonation.

17. Prosthesis according to claim 13, wherein said biocompatible material is a bioartificial material modified and/or treated so as to be biocompatible, and having mechanical characteristics such as to make it suitable for use in artificial cartilage.

\* \* \* \* \*